(12) United States Patent
Pudas et al.

(10) Patent No.: US 11,976,989 B2
(45) Date of Patent: May 7, 2024

(54) SENSOR AND ITS MANUFACTURING METHOD

(71) Applicant: Picosun Oy, Espoo (FI)

(72) Inventors: Marko Pudas, Masala (FI); Jani Kivioja, Masala (FI); Niku Oksala, Masala (FI)

(73) Assignee: PICOSUN OY, Espoo (FI)

( * ) Notice: Subject to any disclaimer, the term of this patent is extended or adjusted under 35 U.S.C. 154(b) by 813 days.

(21) Appl. No.: 16/832,161

(22) Filed: Mar. 27, 2020

(65) Prior Publication Data

US 2020/0309620 A1 Oct. 1, 2020

Related U.S. Application Data

(60) Provisional application No. 62/825,968, filed on Mar. 29, 2019.

(51) Int. Cl.
| | |
|---|---|
| *G01L 1/22* | (2006.01) |
| *A61B 5/00* | (2006.01) |
| *A61B 17/84* | (2006.01) |
| *A61B 17/86* | (2006.01) |
| *H05K 3/46* | (2006.01) |
| *A61B 17/00* | (2006.01) |

(52) U.S. Cl.
CPC .......... *G01L 1/2287* (2013.01); *A61B 5/002* (2013.01); *A61B 5/4851* (2013.01); *A61B 17/846* (2013.01); *A61B 17/86* (2013.01); *H05K 3/4644* (2013.01); *A61B 2017/0003* (2013.01); *A61B 2017/00221* (2013.01); *A61B 2562/0261* (2013.01); *A61B 2562/12* (2013.01)

(58) Field of Classification Search
CPC ......... G01L 1/22; A61B 17/84; A61B 17/846; A61B 17/86; A61B 5/00; A61B 5/002; A61B 5/48; A61B 5/4851; H05K 3/46; H05K 3/4644

See application file for complete search history.

(56) References Cited

U.S. PATENT DOCUMENTS

| | | | |
|---|---|---|---|
| 7,297,591 | B2 | 11/2007 | Won et al. |
| 7,754,563 | B2 | 7/2010 | Nakanishi |
| 9,196,849 | B2 | 11/2015 | Jung et al. |
| 9,919,921 | B2 | 3/2018 | Bright et al. |
| 10,357,651 | B2 | 7/2019 | Pham |

(Continued)

FOREIGN PATENT DOCUMENTS

| | | |
|---|---|---|
| CN | 104714672 A | 6/2015 |
| CN | 1059002346 A | 8/2016 |

(Continued)

OTHER PUBLICATIONS

Byoung H. Lee et al: "Alucone Alloys with Tunable Properties Using Alucone molecular Layer Deposition and Al2O3 Atomic Layer Deposition", Journal of Physical Chemistry C, vol. 116, No. 5, Feb. 1, 2012, 8 Pages.

(Continued)

*Primary Examiner* — Christopher J Beccia
(74) *Attorney, Agent, or Firm* — Espatent Oy

(57) ABSTRACT

A strain sensor that includes a first atomic layer deposition layer, a flexible molecular layer deposition layer on top of the first atomic layer deposition layer, and a second atomic layer deposition layer on top of the molecular layer deposition layer.

11 Claims, 4 Drawing Sheets

(56) References Cited

U.S. PATENT DOCUMENTS

| | | | |
|---|---|---|---|
| 10,558,287 | B2 | 2/2020 | Zhu et al. |
| 2003/0139690 | A1 | 7/2003 | Aebli et al. |
| 2009/0036975 | A1 | 2/2009 | Ward et al. |
| 2009/0104455 | A1 | 4/2009 | Chen et al. |
| 2011/0230747 | A1* | 9/2011 | Rogers ............ A61L 31/047 600/377 |
| 2016/0197292 | A1 | 7/2016 | Lee et al. |
| 2016/0235456 | A1* | 8/2016 | Lao .............. A61B 17/866 |
| 2016/0304341 | A1* | 10/2016 | Bright .............. B82B 3/008 |
| 2016/0354174 | A1* | 12/2016 | Demir .............. A61B 5/686 |

FOREIGN PATENT DOCUMENTS

| | | |
|---|---|---|
| CN | 106456038 A | 2/2017 |
| EP | 2755023 A1 | 7/2014 |
| EP | 3048185 A1 | 7/2016 |
| EP | 3082022 A1 | 10/2016 |
| WO | 2018146146 A1 | 8/2018 |

OTHER PUBLICATIONS

European Patent Office, Partial European Search Report, Application No. 20165498.5, dated May 18, 2020, 17 Pages.

Suk-Won Wang et al: "A Physically Transient Form of Silicon Electronics", Science vol. 337, Aug. 16, 2012, 6 Pages.

European Patent Office, Extended European Search Report, Application No. 20165498.5-1115, dated Aug. 7, 2020, 15 Pages.

Plum et al., "Design of a MEMS Capacitive Chemical Sensor Based on Polymer Swelling", Microelectronics and Electron Devices, XP010935613, DOI: 10.1109/WMED.2006.1678304, ISBN: 978-1-4244-0374-5, Apr. 14, 2006, 2 Pages.

Deivasigamani et al., "A Review of Passive Wireless Sensors for Structural Health Monitoring", Modern Applied Science, vol. 7, No. 2; 2013, ISSN 1913-1844, Published by Canadian Center of Science and Education, Published Online Jan. 29, 2013, doi: 10.5539/mas.v7n2p57, URL: http://dx.doi.org/10.5539/mas.v7n2p57, 20 pages.

* cited by examiner

SENSOR AND ITS MANUFACTURING METHOD

FIELD

The aspects of the disclosed embodiments generally relate to sensors and their manufacturing methods.

BACKGROUND

This section illustrates useful background information without admission of any technique described herein representative of the state of the art.

In medical applications it would be useful to obtain strain information from a human body to obtain performance of an implanted device without expensive imaging. Examples of these applications are tubular mesh-like stents, either uncovered or covered with a cloth used to maintain flow through a tube and to prevent leakage of fluid outside the tube, artificial valves for example in the treatment of cardiovascular diseases, urology and gastroenterology, screws and nails used to fix plates for the treatment of bone fractures or in the stabilization of bone structures in other indications (osteosynthesis). An ultimate challenge is to enable the stent to remain open and allow for unobstructed flow for a maximum period of time after the intervention. However, the insertion of the stent evokes an inflammatory response and tissue repair response which may cause restenosis and ultimately obstruction of the stented area. A critical factor contributing to the risk of restenosis is the kinking or excessive strain of the stent and the stented area resulting in stent wall stress and ultimately loss of stent mechanical integrity. Means to monitor stent strain may enable monitoring of the stent integrity and ability to detect abnormalities and therefore act before stent failure. In case of orthopedic screws and nails, there is need to be able to monitor the biomechanical loading during patient recovery. Too early loading may result in failure of the osteosynthesis and costly reoperation. The osteosynthesis should remain rigid until bone healing has been completed. Means to monitor orthopedic screw and nail strain would enable monitoring of appropriate mechanical loading of the repaired area and therefore control patient recovery maximizing safety.

SUMMARY

It is an object of certain embodiments of the present disclosure to obtain strain information from a human body.

According to a first example aspect of the disclosed embodiments there is provided a strain sensor device as defined in appended patent claim 1.

Embodiments of the first aspect are defined in dependent patent claims.

According to a second example aspect of the disclosed embodiments there is provided a method for manufacturing a strain sensor device as defined in appended patent claim 10.

According to a further example aspect of the disclosed embodiments there is provided strain sensor, comprising:
 a first layer;
 a flexible or compressible molecular layer deposition, MLD, layer on top of the first layer; and
 a second layer on top of the MLD layer.

Embodiments of the present disclosure may be used, for example, in implantable and biodegradable parts.

In certain embodiments, the first and second layer are electrically conductive, or conductors (or form electrodes).

In certain embodiments, the flexible MLD layer is electrically insulating.

In certain embodiments, the first layer and second layer are atomic layer deposition, ALD, layers. Instead of ALD, the first and second layer may be manufactured using another method.

In certain embodiments, at least part of all said three layers overlap, to form an area where deformation of said flexible layer affects the capacitance measured in between the electrically conductive layers (electrodes), which may be made by ALD.

In certain embodiments, there is provided a deformable dielectric of a capacitor, formed with molecular layer deposition.

In certain embodiments, the first atomic layer deposition layer is deposited or attached on a biodegradable substrate, such as a biodegradable screw (e.g., bone screw) or nail. In other embodiments, the substrate is not biodegradable.

In certain embodiments, the MLD layer is biodegradable. In other embodiments, the MLD layer is not biodegradable. In certain embodiments, the first layer, and the second layer each are biodegradable. In other embodiments, the first layer, and the second layer each are not biodegradable.

In certain embodiments, the strain sensor comprises a circuit providing information indicative of strain. Strain may refer to compression or force to a certain direction or to any other direction.

According or to another aspect of the disclosed embodiments there is provided a substrate comprising the strain sensor of the preceding strain sensor aspect or any of its embodiments.

According or to yet another aspect of the disclosed embodiments there is provided a sensor, comprising:
 a molecular layer deposition, MLD, layer in between two electrically conductive layers, at least one of the electrically conductive layers having at least one hole for material to push through to absorb to the MLD layer.

In certain embodiments, the material absorbing to the MLD layer causes a change in the capacitance or in any other electrical property of the capacitor structure.

According or to yet another aspect of the disclosed embodiments there is provided a method for manufacturing a strain sensor, comprising:
 depositing a capacitor structure comprising conductive layer on opposite sides of an MLD layer; and
 providing a circuit comprising the capacitor structure configured to provide information indicative of strain.

According or to yet another aspect of the disclosed embodiments there is provided use of a molecular layer deposition, MLD, layer as a deformable capacitor layer in a sensing circuitry.

According to yet another aspect of the disclosed embodiments there is provided a method for manufacturing a strain sensor, comprising:
 depositing a first atomic layer deposition layer on a substrate;
 depositing a flexible molecular layer deposition layer on top of the first atomic layer deposition layer;
 depositing a second atomic layer deposition layer on top of the molecular layer deposition layer; and
 attaching a circuit to the formed structure configured to provide information indicative of strain.

In certain embodiments, the formed structure is a capacitor structure.

In certain embodiments, the formed structure is at least partially a resistor structure.

According to yet another aspect of the disclosed embodiments there is provided use of a molecular layer deposition, MLD, layer as a deformable capacitor layer in a sensing circuitry.

Different non-binding example aspects and embodiments have been presented in the foregoing. The above embodiments and embodiments described later in this description are used to explain selected aspects or steps that may be utilized in implementations of the present disclosure. It should be appreciated that corresponding embodiments apply to other example aspects as well. Any appropriate combinations of the embodiments can be formed.

BRIEF DESCRIPTION OF THE DRAWINGS

The aspects of the disclosed embodiments will now be described, by way of example only, with reference to the accompanying drawings, in which.

DETAILED DESCRIPTION

The basics of an atomic layer deposition (ALD) growth mechanism are known to a skilled person. ALD is a special chemical deposition method based on the sequential introduction of at least two reactive precursor species to at least one substrate. It is to be understood, however, that one of these reactive precursors can be substituted by energy when using, for example, photon-enhanced ALD or plasma-assisted ALD, for example PEALD, leading to single precursor ALD processes. For example, deposition of a pure element, such as metal, requires only one precursor. Binary compounds, such as oxides can be created with one precursor chemical when the precursor chemical contains both of the elements of the binary material to be deposited. Thin films grown by ALD are dense, pinhole free and have uniform thickness.

The at least one substrate is typically exposed to temporally separated precursor pulses in a reaction vessel to deposit material on the substrate surfaces by sequential self-saturating surface reactions. In the context of this application, the term ALD comprises all applicable ALD based techniques and any equivalent or closely related technologies, such as, for example the following ALD sub-types: plasma-assisted ALD, for example PEALD (Plasma Enhanced Atomic Layer Deposition) and photon-enhanced Atomic Layer Deposition (known also as photo-ALD or flash enhanced ALD).

A basic ALD deposition cycle consists of four sequential steps: pulse A, purge A, pulse B and purge B. Pulse A consists of a first precursor vapor and pulse B of another precursor vapor. Inactive gas and a vacuum pump are typically used for purging gaseous reaction by-products and the residual reactant molecules from the reaction space during purge A and purge B. A deposition sequence comprises at least one deposition cycle. Deposition cycles are repeated until the deposition sequence has produced a thin film or coating of desired thickness. Deposition cycles can also be either simpler or more complex. For example, the cycles can include three or more reactant vapor pulses separated by purging steps, or certain purge steps can be omitted. On the other hand, photo-enhanced ALD has a variety of options, such as only one active precursor, with various options for purging. All these deposition cycles form a timed deposition sequence that is controlled by a logic unit or a microprocessor.

Molecular layer deposition (MLD) is a deposition technique that deposits material on the substrate surfaces by sequential self-saturating surface reactions (like ALD), but in MLD more than one atomic layer, such as a chain of polymer, e.g., an organic polymer chain, is deposited in one cycle.

Figure 1:
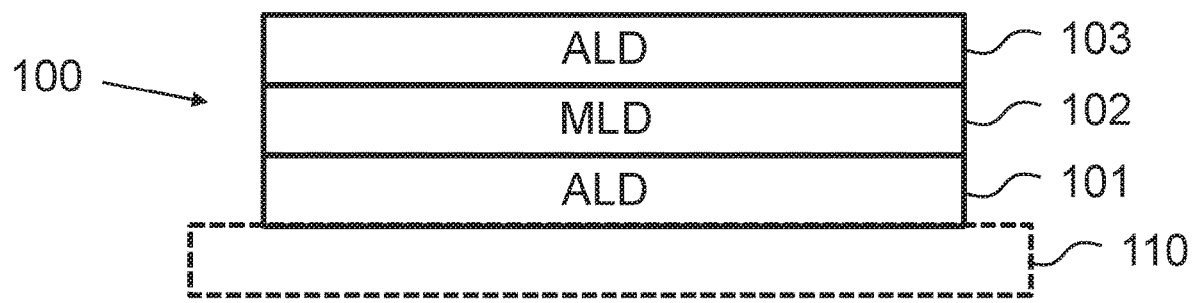
FIG. 1 shows a strain sensor structure in accordance with certain embodiments.

FIG. 1 shows a strain sensor structure 100 manufactured on a substrate 110. The structure comprise a first ALD layer 101 deposited by ALD on the substrate 110, a flexible MLD layer 102 deposited by MLD on the first ALD layer 101, and a second ALD layer 103 deposited by ALD on the MLD layer 102.

The first and second ALD layers 101, 103 are conductors (such as, ZnO doped with $Al_2O_3$, $In_2O_3$, Ru, Pt and/or their combinations) and the flexible MLD layer 102 is of dielectric material i.e. of electrically insulating material (such as, an alucone film or titanicone or zincone). Accordingly, the structure 100 is a capacitor, or an ALD-MLD-ALD capacitor. In certain embodiments, the structure is a capacitor, or an ALD-MLD-ALD capacitor with a (variable) resistance which is or may be affected by mechanical forces or chemical absorption. Another example of dielectric material is $Nb_2O_5$.

In certain embodiments, each of the layers 101-103 and the substrate 110 are biodegradable (but in other embodiments they are not biodegradable, or at least not all of them). The flexible MLD layer 102 contracts (is compressed) or expands when it experiences pressure or release of pressure, respectively. The capacitance of the capacitor structure changes, which can be detected by a radio frequency signal from outside of the body. For example, an LC circuit or an RLC circuit can be formed which is read from the outside (or reflected power is measured). The change in capacitance will change the response of the circuitry. The strain (or compression) experienced by the (coated) substrate, for example a bone screw, nail, or stent, is obtained based on the change of the capacitance. The said change in capacitance can be induced with various means specific to the capacitor dielectric material(s).

Figure 2:
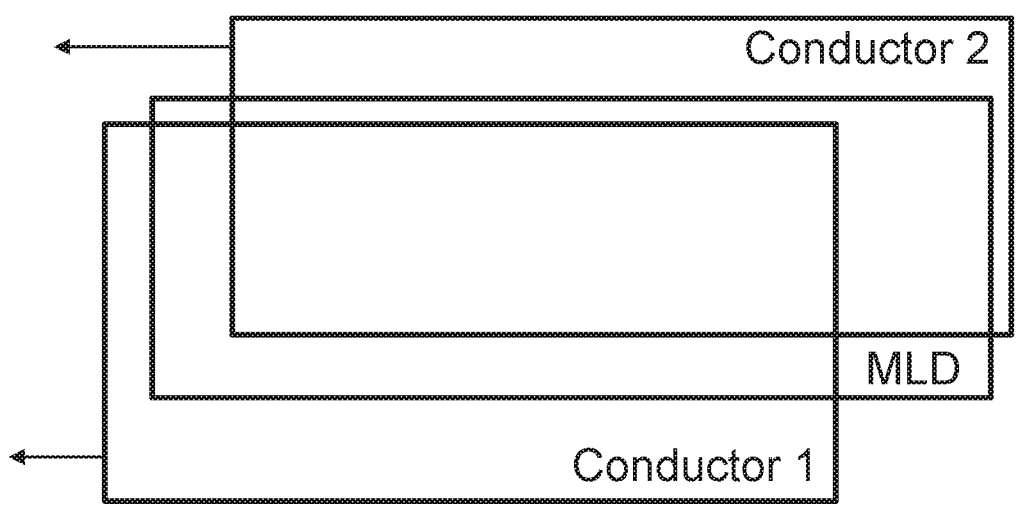
FIG. 2 shows a schematic perspective view of the sensor structure of FIG. 1.

FIG. 2 shows a schematic perspective view of the sensor structure of FIG. 1. FIG. 2 shows the flexible MLD layer in between two electrically conductive layers (Conductor 1, and Conductor 2). The electrically conductive layers have been made by ALD, or by another method. At least part of all said three layers overlap, to form an area where deformation of said flexible layer affects the capacitance measured in between the electrodes (electrically conductive layers). The electrically conductive layers may be provided with conductors (conducting wires or other electric pathways) denoted by arrows in FIG. 2.

Figure 3:
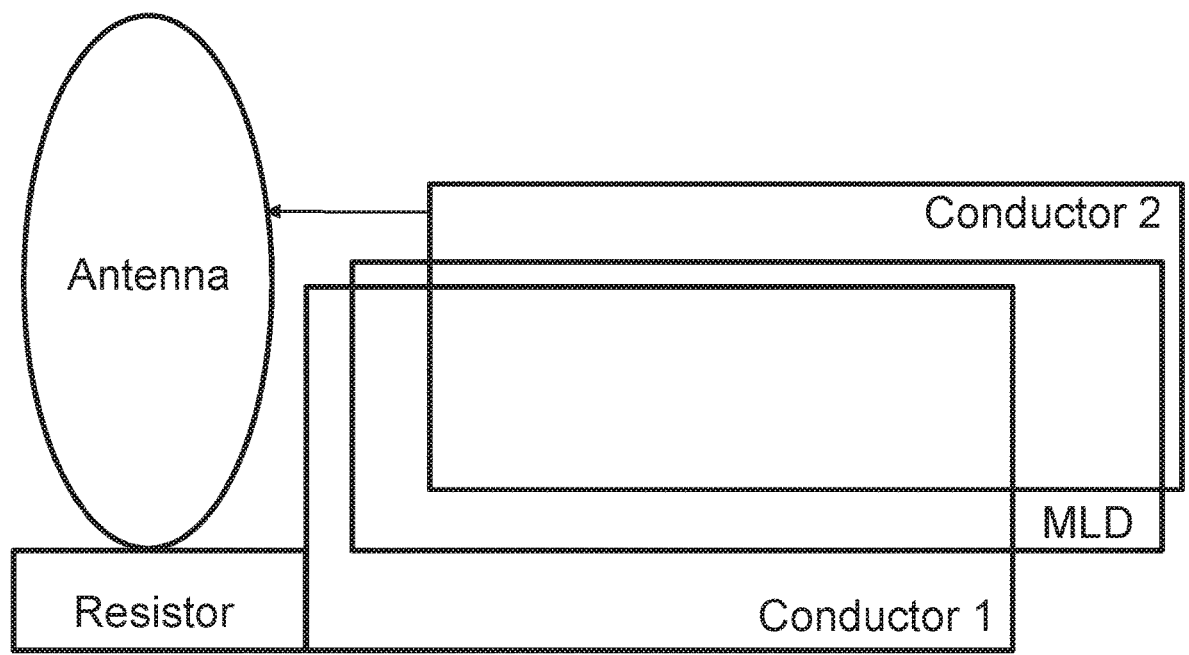
FIG. 3 shows a sensing circuit in accordance with certain embodiments.

FIG. 3 shows a sensing circuit in accordance with certain embodiments. The sensing circuit comprises the capacitor structure (Conductor 1+MLD layer+Conductor 2) with an attached resistor (attached to Conductor 1) and an antenna (attached to Conductor 2 and to the resistor). Accordingly, a sensing circuit is provided. The antenna may be an inductive element (e.g., an inductor), the circuit then being an RLC circuit. The circuit is read from the outside (or reflected power is measured). The strain experienced by the (coated) substrate, for example a bone screw, nail, or stent, is obtained based on the change of the capacitance. The resistor may have been made by ALD.

Figure 4:
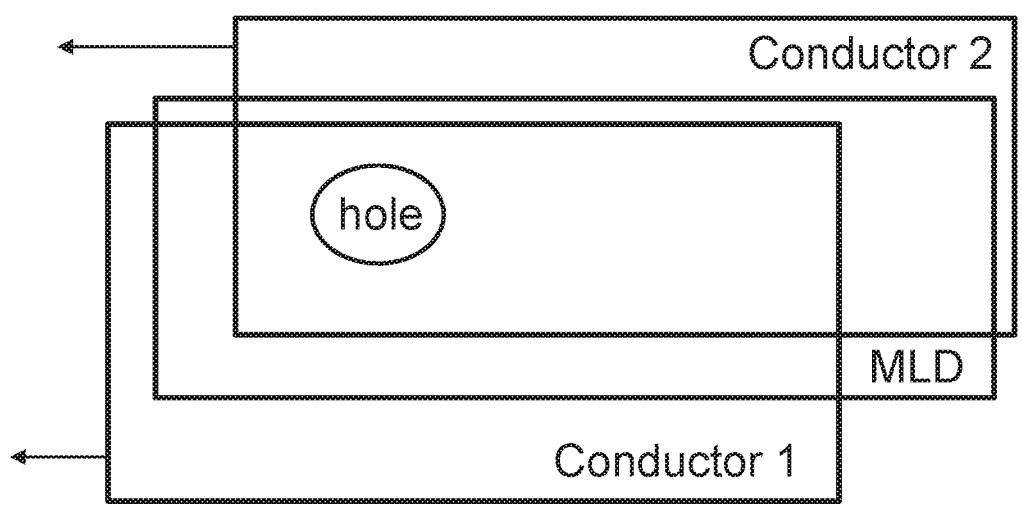
FIG. 4 shows another sensor structure in accordance with further embodiments.

FIG. 4 shows another sensor structure in accordance with further embodiments. The structure shown in FIG. 4 corresponds to that of FIG. 2 except that one of the electrically conductive layers has a hole (or holes) or opening (or openings) through which molecules or ions can go through and absorb to the MLD layer changing the capacitance of the capacitor or its electrical properties, such as electrical conductivity (in an alternative embodiment, said one of the electrically conductive layers has porosity with a similar effect). In that way, the structure can be used e.g. as an ion detector. An RLC circuit can be formed similarly as in FIG. 3 for example.

As to summarize certain embodiments, the embodiments provide an MLD layer used as a dielectric layer of a (variable) capacitor or a variable resistor. The MLD layer is flexible enabling the capacitor (and/or resistive properties) to be adjustable by strain, such as pressure or compression, induced on it or applied to it. In certain embodiments, the MLD layer is biodegradable. It may be made of MLD materials, such as, but not limited to alucone, titanicone and zincone. The performance and properties of the said MLD layer can be modified with doping with other ALD and MLD layers or ALD pulses.

If the implant is conductive, it implant itself can be work, and be connected as antenna.

In certain embodiments, to form a capacitor, the MLD layer is be coated with conductive materials. The conductive materials on both sides of the MLD layer can be made with processes known as such, e.g., $Al_2O_3+ZnO$, conducting biocompatible material. Its resistivity can be adjusted by the ratio of the said materials. There is a vast range of other materials and deposition processes to produce the conductors, too. Thin films are however preferred, in order to have a minimum thickness and impact to the environment where they are used.

Further, the MLD layer can be coated with an electrically insulating layer having a selected thickness, such as ALD deposited $Al_2O_3$.

The capacitor can be used as a part of an RC circuit or an RLC circuit known as such in various wireless communication solutions.

The resistor of the RC or RLC circuit can be made by ALD and with bio decomposable materials.

The antenna, if any, of the RC or RLC circuitry can be made by ALD and with bio decomposable materials.

The circuit (or circuitry) is read with external means, such as antenna inducing RF excitation sufficient to cause included current to the RC circuitry, which is dependent on the varying of capacitance C of the capacitor made with MLD which is deforming, such as compressing for thinner thickness under external load. Variation of the circuitry behavior can be further measured with external means to get an indication of the applied force for example.

In some embodiments, the complete assembly can be at least partially coated by a bio-non-dissolving layer, such as a SiO/HfO laminate, made with ALD or similar, or by any such layer bio-dissolving in significantly longer time than the sensor structure.

In certain embodiments, the capacitance and/or resistance is changed by absorbance of molecules or ions to the MLD layer, which absorption is enabled by surrounding (or adjacent) layer. The surrounding layer (which may be made by ALD) may be transmitting detectable materials, or it may be patterned to have holes for the said transmission of material. The said transmission may also be ion exchange. The said openings can be also further coated with material affecting the transmission of absorbing species.

An advantage obtained by certain embodiments is that the shape of the used bio implant may not be affected while it can be used in measurement of the force induced to it. Further, in some cases, the bio implant screw for example may be intended to decompose, and it is beneficial that the embedded sensors are also decomposed.

Without limiting the scope and interpretation of the patent claims, certain technical effects of one or more of the example embodiments disclosed herein are listed in the following. A technical effect is obtaining strain information from a human body.

The foregoing description has provided by way of non-limiting examples of particular implementations and embodiments of the present disclosure a full and informative description of the best mode presently contemplated by the inventors for carrying out the present disclosure. It is however clear to a person skilled in the art that the present disclosure is not restricted to details of the embodiments presented above, but that it can be implemented in other embodiments using equivalent means without deviating from the characteristics of the present disclosure.

Furthermore, some of the features of the above-disclosed embodiments of this present disclosure may be used to advantage without the corresponding use of other features. As such, the foregoing description should be considered as merely illustrative of the principles of the present disclosure, and not in limitation thereof. Hence, the scope of the present disclosure is only restricted by the appended patent claims.

The invention claimed is:

1. A strain sensor device, comprising:
   a first electrically conductive atomic layer deposition, ALD, layer attached or deposited on a substrate;
   a flexible or compressible electrically insulating molecular layer deposition, MLD, layer on top of the first ALD layer; and
   a second electrically conductive ALD layer on top of the MLD layer, the strain sensor forming a circuit providing information indicative of strain.

2. The device of claim 1 being an implantable device.

3. The device of claim 1, comprising:
   an antenna to provide said information indicative of strain.

4. The device of claim 1, wherein said substrate is biodegradable.

5. The device of claim 1 being biodegradable.

6. The device of claim 1, wherein the substrate is a biodegradable screw or nail.

7. The device of claim 1, comprising an RC or RLC circuit to provide said information indicative of strain.

8. The device of claim 1, wherein the device is configured to provide said information indicative of strain externally readable by radio frequency.

9. A sensor, comprising:
   a molecular layer deposition, MLD, layer in between two electrically conductive atomic layer deposition, ALD, layers, at least one of the electrically conductive ALD layers having at least one hole for material to push through to absorb to the MLD layer.

10. A method for manufacturing a strain sensor device, comprising:
    taking an implantable substrate;
        depositing on the implantable substrate a capacitor structure comprising an electrically conductive ALD layer on opposite sides of a flexible or compressible electrically insulating MLD layer; and providing a circuit comprising the capacitor structure configured to provide information indicative of strain.

11. The method of claim 10, wherein the MLD layer together with the device is biodegradable.

* * * * *